United States Patent [19]

Bombardelli et al.

[11] Patent Number: 5,665,335
[45] Date of Patent: Sep. 9, 1997

[54] COMBINATIONS OF VASOACTIVE SUBSTANCES WITH FATTY ACIDS TO PREVENT HAIR LOSS

[75] Inventors: Ezio Bombardelli; Aldo Cristoni; Paolo Morazzoni, all of Milan, Italy

[73] Assignee: Indena S.A., Milan, Italy

[21] Appl. No.: 498,864

[22] Filed: Jul. 6, 1995

[30] Foreign Application Priority Data

Jul. 19, 1994 [IT] Italy ............................. MI94A1497

[51] Int. Cl.[6] ............................. A61K 7/00; A61K 7/06
[52] U.S. Cl. ............................. 424/70.1; 424/401
[58] Field of Search ............................. 424/401, 70.1, 424/62, 70.8; 514/861, 828, 863, 864, 887, 852, 880, 944

[56] References Cited

U.S. PATENT DOCUMENTS

| | | | |
|---|---|---|---|
| 5,037,803 | 8/1991 | Gueyne et al. | 514/2 |
| 5,523,090 | 6/1996 | Znaiden et al. | 424/401 |

FOREIGN PATENT DOCUMENTS

| | | |
|---|---|---|
| 0 680 761 A1 | 6/1994 | European Pat. Off. . |
| 0 680 761 A1 | 4/1995 | European Pat. Off. . |

*Primary Examiner*—Thurman K. Page
*Assistant Examiner*—Sharon Howard
*Attorney, Agent, or Firm*—Pennie & Edmonds

[57] ABSTRACT

The present invention relates to novel formulations useful in the preventive and curative treatment of hair loss and of seborrhea, containing coumarins such as khellin, visnadin, esculoside or alkaloids such as raubasine, vincamine and derivatives thereof, combined with unsaturated and saturated fatty acids.

22 Claims, No Drawings

COMBINATIONS OF VASOACTIVE SUBSTANCES WITH FATTY ACIDS TO PREVENT HAIR LOSS

TECHNICAL FIELD

The present invention relates to novel formulations useful in the preventive and curative treatment of hair loss, containing combinations of substances activating the microcirculation of "galea capitis" and products having antiseborrhoic and antiandrogen actions. It has surprisingly been found that formulations containing coumarins such as khellin, visnadin, esculoside, or alkaloids such as raubasine, vincamine and derivatives thereof, combined with unsaturated fatty acids such as ximenynic acid, the ethyl ester or other esters thereof, as well as acids such as lauric, myristic or isomyristic acids, are synergistically active in stimulating hair regrowth or in preventing its loss.

BACKGROUND OF THE INVENTION

The vasokinetic activity of some of these substances, such as visnadin and khellin, have already been described in Patent application IT-21786A/89, which evidenced the effect thereof on the increase in the volume and in the blood flow rate at the level of the capillary network, and the use of these substances in peripheral vasculopathies and in primitive and secondary alopecias had been provided. Similarly, ximenynic acid free or in the form of triglyceride and generally of esters, was found to increase the blood flow with mechanisms different from those of visnadin and khellin (Patent IT-1223290).

SUMMARY OF THE INVENTION

The present invention provides a composition for the prevention and curative treatment of hair loss and seborrhea, which comprises at least one fatty acid or fatty acid ester, and at least one coumarin, alkaloid, or alkaloid derivative or a combination thereof. These active ingredients may be present in a liquid carrier, such as an alcohol, or in the form of a gel. The present invention also provides a method of preventing or curing hair loss or seborrhea, which includes forming a composition, which comprises at least one fatty acid or fatty acid ester, and at least one coumarin, alkaloid, alkaloid derivative, or a combination thereof, and topically applying a functional amount of the liquid or gel composition to a patient or subject.

DETAILED DESCRIPTION OF THE INVENTION

The present invention relates to a composition and method for the prevention and curative treatment of hair loss and seborrhea. The claimed composition comprises at least one fatty acid or fatty acid ester, such as ximenynic acid, a ximenynic acid ester, a saturated $C_{12}$–$C_{14}$ acid, or a saturated $C_{12}$–$C_{14}$ acid ester, and at least one coumarin, such as khellin, visnadin, esculoside, or esculetin, or an alkaloid or alkaloid derivative, such as raubasine, vincamine, or a derivative thereof. The composition may also contain a mixture of at least one coumarin and at least one alkaloid or alkaloid derivative in addition to the fatty acid. In the method of the present invention, the claimed composition is topically applied to a patient or a subject to prevent or cure hair loss or seborrhea.

Ximenynic acid and the esters thereof, when applied topically for a long time, exert a double effect at the cutaneous level: a microvasculokinetic one and antiseborrhoic one. Such two actions combined in the same molecule are particularly useful for keeping the skin effectively vascularized and at the same time dry thanks to a decreased sebum secretion. $C_{12}$ and $C_{14}$ acids, such as lauric, myristic and isomyristic acids, turned out to be strong inhibitors of dihydrotestosterone receptor binding, therefore, when suitably carried through the epicutaneous layer, they can exert a remarkable antiandrogen action, thus, contributing to a sebaceous regulation.

The combination of substances with vasokinetic activity (coumarins or alkaloids) with unsaturated fatty acids or the esters thereof as antiseborrhoic agents and with $C_{12}$ and $C_{14}$ acids with antiandrogen activity is one of the objects of the invention, and is proved to be particularly useful for stimulating the hair follicle and keeping the skin nourished thanks to a higher supply of blood, and, therefore, of trophic substances. As a result, after a few days of treatment, a marked change in the skin occurs, with an increased number of perfused capillaries and an absence of dandruff; hair follicles are normal and patent, and the sebum production is normal.

The above mentioned products, when combined together, are suitable for the administration in the form of hydroalcoholic lotions (which are those preferred for treatments of the scalp,) or in the form of gels.

The preferred combinations for said treatments contain a combination of visnadin or khellin, in concentrations ranging from 0.2% to 3%; preferably 1 to 2% ximenynic acid or esters thereof, in concentrations ranging from 0.2% to 10% (preferably 0.5 to 1.5%); and lauric acid in concentrations ranging from 0.1% to 1% (preferably 0.2 to 0.5%).

In typical treatment, about 0.1 to about 1 g, and preferably 0.5 g of a lotion or gel of this formulation is applied topically. Visnadin and khellin can advantageously be replaced by esculoside or by its aglucon esculetin, in concentrations varying from 0.3% to 4% (preferably 1 to 2%). Typically, about 0.1 to about 1 g, preferably 0.5 g of a lotion or gel containing esculoside or esculetin is applied topically.

Esculoside, in combination with ximenynic acid and the esters thereof and lauric, myristic and isomyristic acids, is particularly suitable for the treatment of early hair loss and for the stimulation of hair growth. These components are used in combinations in the amounts described above. The balance of the formulation contains a liquid carrier, such as an alcohol, preferably ethyl alcohol, optionally in combination with about 1 to about 20 weight percent of a siloxane compound or mixture of siloxane compounds. The treatment with these substances can vary from a few days to 6 months. About 0.1 to 1 g of the compositon is applied to the subject each day to assure that therapeutically effective amounts of the active ingredients are delivered.

PHARMACOLOGICAL EXPERIMENTATION

EXAMPLES

The following non-limiting examples are merely illustrative of the preferred embodiments of the present invention, and are not to be construed as limiting the invention, the scope of which is defined by the appended claims.

30 Subjects with primary or secondary alopecia were subdivided into 3 groups of 10 individuals each and treated for 90 days respectively with:

Group 1: a formulation containing 1% esculoside;

Group 2: a formulation containing 0.5% ximenynic acid and 0.2% lauric acid;

Group 3: a formulation containing 1% esculoside, 0.5% ximenynic acid and 0.2% lauric acid.

Each treatment included the application of about 0.5 g of a lotion or gel of the formulation. Treatments were performed at least once a day during the 90 day test.

The vasokinetic effects and those on trichogram were evaluated both at the beginning and the end of the treatment.

Trichogram (basal and after 90 days) consists in withdrawing a suitale number (about 50) of hairs by means of rubberized tweezers, both at the frontal-superior and lateronuchal areas (Bosse K., Hautzart, 18, 35, 1967; Bosse K., Hautzart 18, 218, 1967).

Microscope observation of hair roots allows to evaluate the percentage of hair in anagen (growth), catagen (mature) or telogen (latency) phases. A telogen percentage higher than 10–15% (which is considered normal) gives a clinical evidence of a pathological condition of hair loss (Mortimer C. H., Rushton H., James K. C., Clin. Exp. Dermatol., 9, 342, 1984).

The vasokinetic effects were tested using the laser-Doppler flowmetry (Nilsson G. E., Tenland T., Oberg P. A., IEEE Transaction Biochem. Eng., 27, 12, 1980) using the PeriFlux$^R$ PF3 flowmeter. This technique made it possible to measure the blood flow of the scalp of the subjects under test, under basal conditions and after administration of the test formulations, 15 minutes after the first administration (acute effect) and 8 hours after the administration, at the 30th, 60th and 90th day of treatment.

The results reported in Table 1 show the efficacy of esculoside as a vasokinetic agent.

The combination of said compound with ximenynic and lauric acids exerts a significant action on the hair follicle, so as to synergistically stimulate the regrowth or decrease the hair loss (13% telogen after a 90 day treatment), compared with the administration of the single components (Table 2).

| 100 g of lotion contain: | |
|---|---|
| Esculoside | 0.30 g |
| Ximenynic acid | 0.50 g |
| Lauric acid | 0.20 g |
| Butylhydroxytoluene | 0.10 g |
| Ethyl alcohol 50° | q.s. to 100 ml |

EXAMPLE II

Lotion containing visnadin, ximenynic acid ethyl ester and lauric acid.

| | |
|---|---|
| Visnadin | 1.00 g |
| Ximenynic acid ethyl ester | 10.00 g |
| Lauric acid | 1.00 g |
| 80/20 Tetrameric cyclosiloxane and pentameric cyclosiloxane mixture (SF 1204 - GE silicones) | 15.00 g |
| Ethanol 95° | q.s. to 100 ml |

While it is apparent that the invention herein disclosed is well calculated to fulfill the objects above stated, it will be appreciated that numerous modifications and embodiments may be devised by those skilled in the art. It is intended that the appended claims cover all such modifications and

TABLE 1

Effects on the average capillary blood flow induced by the topical administration of esculoside (group 1), ximenynic acid + lauric acid (group 2) and esculoside + ximenynic acid + lauric acid (group 3).

| | Capillary flow (AU ± s.e.) | | | | |
|---|---|---|---|---|---|
| Treatment | Basal | 15 minutes | 30 days | 60 days | 90 days |
| Group 1 | 9.2 ± 1.0 | 23.1 ± 3.0* | 11.7 ± 2.4 | 16.8 ± 1.2* | 16.7 ± 1.1* |
| Group 2 | 9.4 ± 1.2 | 10.0 ± 1.3 | 10.7 ± 1.5 | 11.0 ± 1.1 | 11.5 ± 0.9 |
| Group 3 | 9.3 ± 1.1 | 24.0 ± 3.1* | 12.1 ± 2.5 | 17.1 ± 1.3* | 16.4 ± 1.0* |

* = $p < 0.01$ vs. basal in the variance analysis of a split-plot design (Bonferroni t test)
N = 10

TABLE 2

Effects on trichogram induced by the topical administration (90 days) of esculoside (group 1), ximenynic acid + lauric acid (group 2) and esculoside + ximenynic acid + lauric acid (group 3).

| | | Trichogram (% − m ± s.e.) | |
|---|---|---|---|
| Treatment | | anagen + catagen | telogen |
| Group 1 | Before | 76 ± 3 | 24 ± 1 |
| | After 90 days | 79 ± 3 | 21 ± 1 |
| Group 2 | Before | 78 ± 2 | 22 ± 1 |
| | After 90 days | 80 ± 2 | 20 ± 1 |
| Group 3 | Before | 75 ± 2 | 25 ± 1 |
| | After 90 days | 87 ± 3* | 13 ± 1* |

*= $p < 0.01$ vs. basal based on the calculation of the Student t for paired data.
N = 10.

Examples of formulations useful for the treatment of scalp will be shown in the following non-limiting examples.

EXAMPLE I

Lotion containing esculoside, ximenynic acid and lauric acid.

embodiments as fall within the true spirit and scope of the present invention.

What is claimed is:

1. A composition for the treatment of hair loss and seborrhea, comprising a therapeutically effective amount of the combination of (1) at least one fatty acid or fatty acid ester, and (2) at least one coumarin, alkaloid, alkaloid fatty acid, alkaloid ester, or combination thereof.

2. The composition according to claim 1, wherein:
the fatty acid or fatty acid ester is ximenynic acid, a saturated $C_{12}$–$C_{14}$ acid, a ximenynic acid ester, or a saturated $C_{12}$–$C_{14}$ acid ester,
the coumarin is khellin, visnadin, esculoside, or esculetin, and
the alkaloid is raubasine, vincamine, or a fatty acid or ester thereof.

3. The composition according to claim 1, comprising a mixture of esculoside, ximenynic acid, and lauric acid.

4. The composition according to claim 1, comprising a mixture of visnadin, ximenynic acid ethyl ester, and lauric acid.

5. The composition of claim 1, which further comprises a liquid carrier so that the composition is in the form of a lotion or gel.

6. A composition for the treatment of hair loss and seborrhea, comprising about 0.2% to about 3% of visnadin or khellin, about 0.2% to about 10% of ximenynic acid or a ximenynic acid ester, and about 0.1% to about 1% of lauric acid.

7. The composition according to claim 6, comprising about 0.5 to 1.5% of ximenynic acid or ester thereof and about 0.2 to 0.5% of lauric acid.

8. A composition for the treatment of hair loss and seborrhea, comprising about 0.3% to about 4% of esculoside or esculetin, about 0.2% to about 10% of ximenynic acid or an ester thereof, and about 0.1% to about 1% of lauric acid.

9. The composition according to claim 8, wherein the composition comprises about 1 to 2% of esculoside or esculetin, about 0.5 to 1.5% of ximenynic acid or ester thereof, and about 0.2 to 0.5% of lauric acid.

10. A method for the treatment of hair loss or seborrhea, comprising applying to a subject a therapeutically effective amount of a composition comprising the combination of (1) at least one fatty acid or ester thereof, and (2) at least one coumarin, alkaloid, alkaloid fatty acid, alkaloid ester, or combination thereof.

11. The method according to claim 10, wherein:

the fatty acid or ester is ximenynic acid, a saturated $C_{12}$–$C_{14}$ acid, a ximenynic acid ester, a saturated $C_{12}$–$C_{14}$ acid ester, or a mixture thereof, the coumarin is khellin, visnadin, esculoside, esculetin, or a mixture thereof, and the alkaloid is raubasine, vincamine, a fatty acid or ester thereof, or a mixture thereof.

12. The method according to claim 10, wherein the composition comprises the combination of esculoside, ximenynic acid, and lauric acid.

13. The method according to claim 10, wherein the composition comprises the combination of visnadin, ximenynic, acid ethyl ester, and lauric acid.

14. The method according to claim 10, which further comprises adding a liquid carrier to the composition to form a lotion or gel to facilitate application thereof.

15. The method according to claim 10, wherein the composition comprises about 0.2% to about 3% of visnadin or khellin, about 0.2% to about 10% of ximenynic acid or an ester thereof, and about 0.1% to about 1% of lauric acid.

16. The method according to claim 12, wherein the composition comprises about 0.5 to 1.5% of ximenynic acid or ester thereof and about 0.2 to 0.5% of lauric acid.

17. The method according to claim 10, wherein the composition comprises about 0.3% to about 4% of esculoside or esculetin, about 0.2% to about 10% of ximenynic acid or an ester thereof, and about 0.1% to about 1% of lauric acid.

18. The method according to claim 17, wherein the composition comprises about 1 to 2% of esculoside or esculetin, about 0.5 to 1.5% of ximenynic acid or ester thereof, and about 0.2 to 0.5% of lauric acid.

19. The method of claim 10, further comprising treating the scalp of the subject with the composition for a period of about 2 days to about 6 months.

20. The method of claim 10, wherein an amount of about 0.1 to about 1 g of the composition is applied to the subject each day.

21. The composition of claim 1 further comprising lauric acid in an amount effective to enhance the therapeutic effect of the combination of components (1) and (2).

22. The method of claim 10, where the composition to be applied also contains lauric acid in an amount effective to enhance the therapeutic effect of the combination of components (1) and (2).

* * * * *